(12) United States Patent
Shinno et al.

(10) Patent No.: US 9,103,772 B2
(45) Date of Patent: Aug. 11, 2015

(54) BODY FOR STORING BIOSENSORS AND MEASUREMENT DEVICE USING THE BIOSENSORS

(75) Inventors: Teppei Shinno, Ehime (JP); Hiroyuki Tokunaga, Ehime (JP); Tomoharu Yamamura, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 29 days.

(21) Appl. No.: 13/821,437

(22) PCT Filed: Sep. 30, 2011

(86) PCT No.: PCT/JP2011/005545
§ 371 (c)(1),
(2), (4) Date: Mar. 7, 2013

(87) PCT Pub. No.: WO2012/042904
PCT Pub. Date: Apr. 5, 2012

(65) Prior Publication Data
US 2013/0168276 A1 Jul. 4, 2013

(30) Foreign Application Priority Data
Sep. 30, 2010 (JP) ................................ 2010-221136

(51) Int. Cl.
*G01N 27/327* (2006.01)
*G01N 33/487* (2006.01)
*A61B 19/02* (2006.01)
*G01N 33/48* (2006.01)

(52) U.S. Cl.
CPC ............ *G01N 27/327* (2013.01); *A61B 19/026* (2013.01); *G01N 33/48* (2013.01); *G01N 33/48778* (2013.01)

(58) Field of Classification Search
USPC ........................................ 204/403.01–403.15
See application file for complete search history.

(56) References Cited

U.S. PATENT DOCUMENTS

| | | |
|---|---|---|
| 2003/0144608 A1 | 7/2003 | Kojima et al. |
| 2003/0159945 A1 | 8/2003 | Miyazaki et al. |
| 2005/0178663 A1 | 8/2005 | Kobayashi |
| 2009/0084687 A1 | 4/2009 | Chatelier et al. |

FOREIGN PATENT DOCUMENTS

| | | |
|---|---|---|
| CN | 1629630 A | 6/2005 |
| JP | 2006-188255 A | 7/2006 |

(Continued)

OTHER PUBLICATIONS

International Search Report for PCT/JP2011/005545 dated Nov. 8, 2011.

(Continued)

*Primary Examiner* — J. Christopher Ball
(74) *Attorney, Agent, or Firm* — Pearne & Gordon LLP

(57) ABSTRACT

The purpose of the present invention is to facilitate the extraction of plate-shaped biosensors stored in a container body. More specifically, a body for storing biosensors is provided, the body including: a tube-shaped storage container body having an open upper face; a lid body for covering the upper face opening of the storage container body so that the lid can open and close the upper face opening; and plate-shaped biosensors stored within the tube-shaped container body. The biosensors are each provided with a measurement section disposed at one end thereof; a connection terminal section disposed at the other end thereof; and a connection section disposed between the one end and the other end and electrically connecting the measurement section and the connection terminal section. The biosensors each have a protrusion disposed at an end thereof in the longitudinal direction thereof.

2 Claims, 13 Drawing Sheets

(56) References Cited

FOREIGN PATENT DOCUMENTS

| | | |
|---|---|---|
| JP | 2009-85950 A | 4/2009 |
| JP | 2010-127786 A | 6/2010 |
| JP | 2010-148898 A | 7/2010 |
| WO | 03/076918 A1 | 9/2003 |
| WO | 2005/108968 A1 | 11/2005 |

OTHER PUBLICATIONS

English translation of Search Report for Chinese Application No. 201180047194.5 dated Oct. 28, 2014.

BODY FOR STORING BIOSENSORS AND MEASUREMENT DEVICE USING THE BIOSENSORS

TECHNICAL FIELD

The present invention relates to a biosensor container assembly having biosensors such as blood glucose sensors contained in a container, and a measuring apparatus using such biosensors.

BACKGROUND ART

As shown in FIG. 13, a conventional biosensor (blood glucose sensor 5) is plate-shaped and includes measuring section 1 at one end, connecting terminal section 2 at the other end, and connecting section 3 that connects together measuring section 1 and connecting terminal section 2 (connection section 3 has electrical interconnects though they are not shown in the drawing) (see e.g., PTL 1). Measuring section 1 typically has electrodes including a working electrode and a counter electrode, and connecting terminal section 2 has a pair of terminals to be connected to a measuring apparatus, with the electrodes and the terminals being electrically connected via connecting section 3. The terminals of connecting terminal section 2 are for connection to a measuring apparatus.

As shown in FIG. 15, another example of the conventional biosensor (blood glucose sensor 5) has a plate-shaped sensor and includes on one end working electrode 50, counter electrode 51, and information carrier 52 (see, e.g., PTL 2),

CITATION LIST

Patent Literature

PTL 1
Japanese Patent Application Laid-Open No. 2006-188255
PTL 2
WO2003/076918

SUMMARY OF INVENTION

Technical Problem

Conventional biosensors 5 are contained and stored together in a container as shown in FIG. 14. When using biosensor 5, a user picks up one of biosensors 5 in the container. The user then inserts the picked-up bio sensor 5 into an insertion opening of a measuring apparatus (not shown), while the side of connecting terminal section 2 facing the insertion opening, and applies a droplet of blood on measuring section 1. Measuring means of the measuring apparatus then measures the blood glucose level and a measured value is displayed on a display section.

However, the problem is that picking up one of biosensors 5 contained in the container is very cumbersome. Since conventional biosensors 5 are plate-shaped as shown in FIG. 13, the plurality of biosensors 5 contained in the container overlap with each other as shown in FIG. 14. It is troublesome for the user to pick up one plate-shaped biosensors 5 from the container, the biosensors 5 being overlapped in such a manner one by one. The user may pick up two or more biosensor 5 at a time and may accidentally drop one or more of them.

Thus, the user must pick up one of the plate-shaped biosensors from the container slowly and carefully, which is inconvenient. Under these circumstances, the claimed invention is directed to allow the plate-shaped biosensors contained in the container to be picked up readily.

Solution to Problem

In order to achieve at least one of the objects mentioned above, the claimed invention optimized the shape of biosensors and provides a biosensor container assembly having optimally shaped biosensors which are contained in a container in a suitable manner. Thereby, the desired objects are achieved.

Namely, a biosensor container assembly reflecting a first aspect of the claimed invention is as follows:

[1] A biosensor container assembly including: a tubular container body having a top opening, a lid body that covers openably/closably the top opening of the container body; and a plurality of plate-shaped biosensors contained in the tubular container body, wherein each of the biosensors comprises a measuring section disposed at one end, a connecting terminal section disposed at the other end, and a connecting section disposed between the one end and the other end to electrically connect the measuring section and the connecting terminal section, and wherein each of the biosensors comprises a protrusion disposed at a longitudinal end thereof, and the biosensors are contained with the protrusion facing a bottom of the container body.

[2] The biosensor container assembly according to [1], wherein each of the biosensors further comprises a cutout disposed on at least one of opposite sides of the protrusion.

[3] The biosensor container assembly according to [1], wherein the bottom of the container body is close-ended.

[4] The biosensor container assembly according to [1], wherein the measuring section comprises a pair of electrodes composed of a working electrode and a counter electrode, and wherein the connecting terminal section comprises a pair of terminals that electrically connect with the pair of electrodes via the connecting section.

A biosensor container assembly reflecting a second aspect of the claimed invention is as follows:

[5] A measuring apparatus having an insertion opening configured to allow the biosensor according to claim 1 to be inserted therein with the connecting terminal section facing the insertion opening, the measuring apparatus including: a connector connected to a terminal of the connecting terminal section when the biosensor is inserted; a measuring section that measures a specific component based on an output from the measuring section; and a display section that displays a measured result by the measuring section.

[6] The measuring apparatus according to [5], further including a switching section that is configured to be switched by a protrusion provided on the connecting terminal section when the biosensor is inserted.

Advantageous Effects of Invention

In the biosensor container assembly of the claimed invention, the shape of biosensors contained in a container and the manner in which the biosensors are contained in the container are both optimized, so that the biosensors can be readily picked up one by one from the container.

Specifically, the biosensor in the claimed invention is plate-shaped, wherein the biosensor 1) has a protrusion disposed at a longitudinal end thereof, and 2) is contained in the container with the protrusion facing the bottom of a container body. With this configuration, a plurality of biosensors is contained randomly in the container, so that the biosensors can be readily picked up one by one from the container.

In addition, the protrusion of the biosensor can switch a switching section of the measuring apparatus. Thus, the measuring apparatus can determine the type of biosensor according to the protrusion.

In the manner described above, the claimed invention can simplify the test conducted by the users of the biosensors and allow the measuring apparatus to determine the type of biosensor, preventing the false measured results from being provided to the users as well.

BRIEF DESCRIPTION OF DRAWINGS

FIG. 6A is a perspective view of a measuring apparatus having the blood glucose sensor of FIG. 1 inserted therein, an.

DESCRIPTION OF EMBODIMENTS

A biosensor container assembly of the claimed invention includes a container body, a lid body, and a plurality of plate-shaped biosensors.

Container Body

The container body is typically a tubular container having an opening on the top thereof. The bottom of the container body is typically closed. Preferably, the container body protects biosensors contained therein from the external moisture. Although the material of the container body is not limited specifically, it is preferably low vapor permeable and it can be resin and/or the like. A moisture absorbent may be placed inside the container body. The moisture absorbent absorbs moisture penetrated into the container so as to prevent the biosensors contained therein from deterioration due to the moisture.

Although the shape of the container body is not limited specifically as long as it is able to contain the biosensors therein, it is preferably tubular, which can be cylindrical, rectangular tubular, or the like. The inner height of the tubular container body may be configured to be larger than the longitudinal dimension of the biosensor; the inner height being typically 40 to 60 mm.

Lid Body

Figure 4:
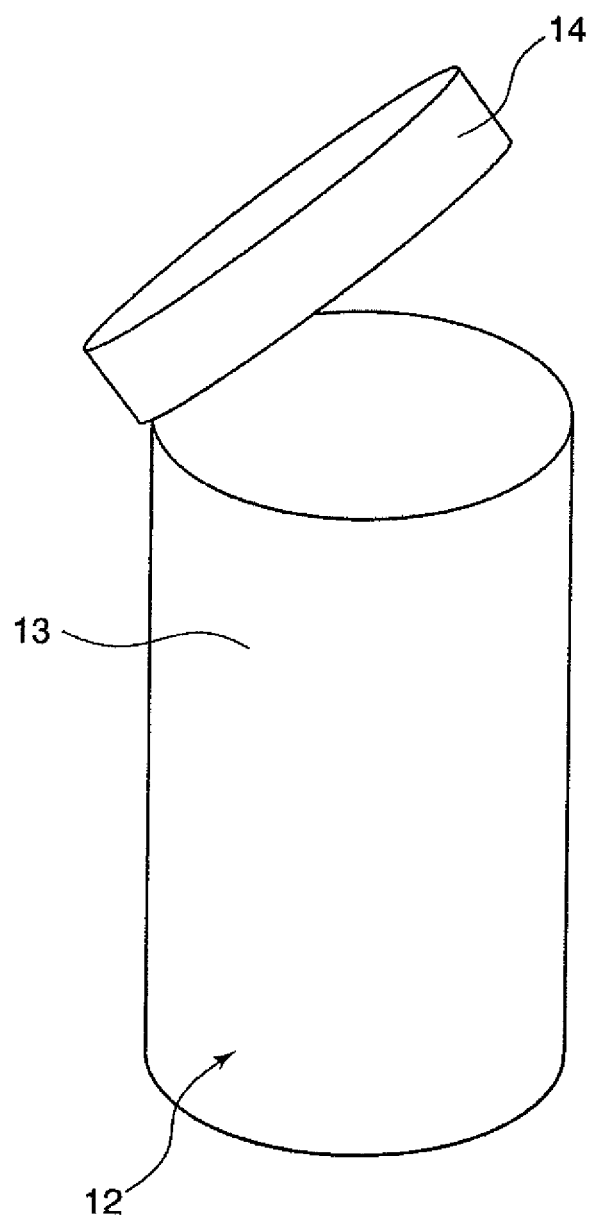
FIG. 4 is a perspective view of a container for containing the blood glucose sensor.

The lid body is a member that covers (seals) the top opening of the container body, and is preferably an openable/closable member. The container sealed with the lid body is preferably sealed air-tight to prevent entry of external moisture and/or oxygen. The lid body may be a separable member from the container body, or may be coupled integrally to the container body as shown in FIG. 4. A moisture absorbent may also be placed on the lid body.

Biosensor

The biosensor is an analyzing tool for measuring the concentration of a specific component in a sample, e.g., blood glucose. The biosensor is preferably plate-shaped, and more preferably is plate-shaped having longitudinal and lateral dimensions. The term "plate-shaped" means that the thickness is 0.05 to 1.0 mm. Although the size of the biosensor is not limited specifically, it is preferred that the longitudinal dimension is 10 mm to 50 mm and the aspect ratio (longitudinal dimension/lateral dimension) is 2 to 16.

Figure 1A:
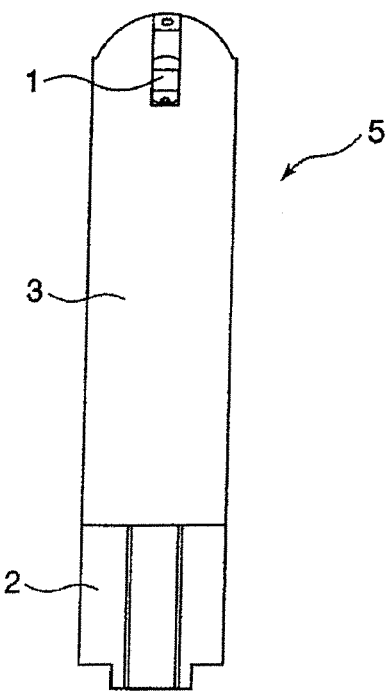
FIGS. 1A and 1B are front and exploded perspective views, respectively, of a blood glucose sensor according to one embodiment of the claimed invention.

The biosensor has a measuring section that measures the amount of a component in the sample, a connecting terminal section having connecting terminals for connection to an analyzing apparatus, and a connecting section that electrically connects together the measuring section and the connecting terminal section (see FIG. 1A). The biosensor also includes a cover, a spacer, and a base, for example (see FIG. 1B).

Figure 2:
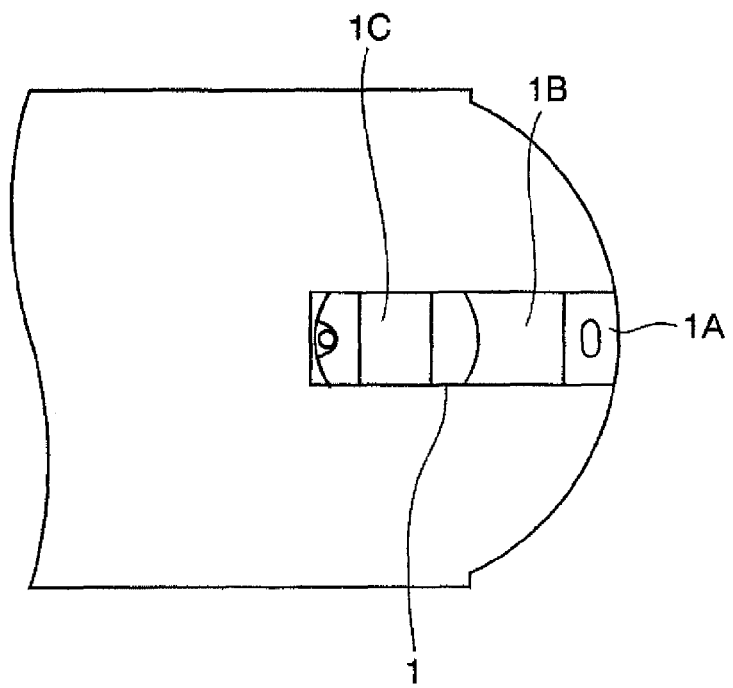
FIG. 2 is an enlarged front view of a measuring section of the blood glucose sensor of FIG. 1.

The measuring section includes an inlet to introduce a sample into the measuring section, a pair of electrodes composed of a working electrode and a counter electrode, a reagent layer, and a guide path that guides the introduced sample to the reagent layer (see FIG. 2). Of course, it may also have electrodes other than the working and counter electrodes, such as a sensing electrode.

The measuring section, particularly the inlet thereof, is preferably positioned at an end of the biosensor. This is to facilitate introduction of sample. The end of the biosensor may be either a longitudinal or lateral end. When the sample is liquid, the guide path preferably has a diameter small enough to cause the capillary action.

Figure 1B:
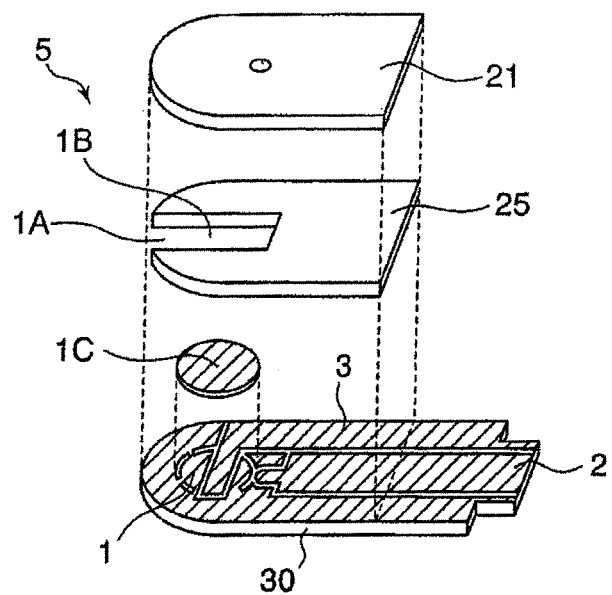

The inlet and the guide path are gaps formed by the cover, the spacer, and the base (see FIG. 1B).

The reagent layer is typically solid and dissolves into the liquid sample. The composition of the reagent layer varies depending on the measurement target. Generally, the reagent layer contains an electron carrier (mediator) and an oxidoreductase. When the measurement target is glucose, examples of the electron carrier include iron complex (such as ferrocene), and ruthenium complex, and examples of the oxidoreductase include glucose dehydrogenase, and glucose oxidase.

The measuring section has a pair of electrodes composed of the working electrode and the counter electrode. The sample dissolves the reagent layer to form a solution, which in turn contacts with the pair of electrodes, and then the pair of electrodes applies voltage to the solution. By, for example, measuring the current flowing through the solution at that time, the amount of a specific component contained in the sample is measured. Thus, the reagent layer is preferably placed near the pair of electrodes.

The measuring section may have other electrodes than the pair of electrodes composed of the working electrode and the counter electrode. For example, the measuring section may have a sensing electrode, or a hematocrit electrode when the sample is blood. The sensing electrode determines whether the sample has been guided to a predetermined position in the measuring section. The hematocrit electrode measures the blood hematocrit level (a value indicating the volume percentage of blood cells in blood). The hematocrit level is used to correct the measured result of a specific component.

The connecting terminal section has connecting terminals that electrically connect the biosensor to the measuring apparatus body. The connecting terminals include at least a pair of terminals composed of a terminal electrically connected with the working electrode of the measuring section and a terminal electrically connected with the counter electrode of the measuring section. When the measuring section has other electrodes, the connecting terminal section also has other terminals electrically connected with the other electrodes.

The connecting terminal section is preferably placed at an end of the biosensor other than the end where the measuring section is placed. Although the end may be either a longitudinal or lateral end, the connecting terminal section is often placed at a longitudinal end.

Each terminal of the connecting terminal section can be electrically connected to the measuring apparatus when the bio sensor is mounted to the measuring apparatus. For example, connectors provided in the measuring apparatus are connected to the respective terminals of the connecting terminal section.

The connecting section electrically connects the measuring section with the connecting terminal section. More specifically, the connecting section means interconnects that electrically connect the respective electrodes (the pair of electrodes and other electrodes) provided in the measuring section with the respective terminals of the connecting terminal section.

Each electrode of the measuring section, each terminal of the connecting terminal section, and the interconnects constituting the connecting section are a patterned conductive film (e.g. metal film) on the base. They may be formed by applying a conductive paste on the base or etching (laser-etching or the like) the conductive film deposited on the base.

The connecting terminal section may include a patterned conductive film other than the terminals. With a predetermined patterning, the type of biosensor can be discriminated according to the connectors as described below (see FIG. 12).

Figure 3:
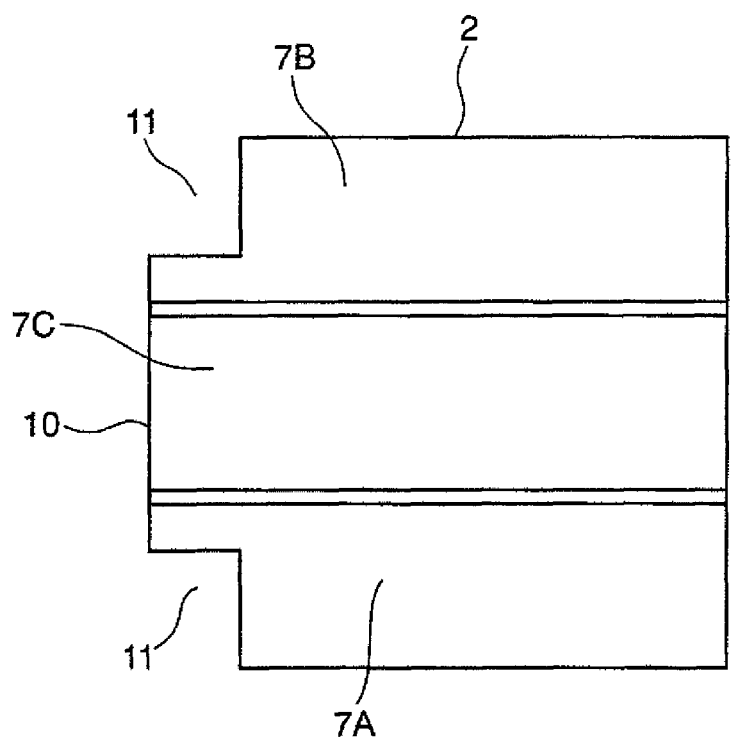
FIG. 3 is an enlarged front view of a connecting terminal section of the blood glucose sensor of FIGS. 1A and 1B.

The biosensor of the claimed invention is characterized by having a protrusion at a longitudinal end (see FIG. 3). In addition, the biosensor preferably has a cutout on at least one of the opposing sides of the protrusion. The protrusion and the cutout may be disposed at a longitudinal end, and are typically integrated with the connecting terminal section. Moreover, the protrusion preferably protrudes along the direction to insert the biosensor into the measuring apparatus.

Figures 1, 11:
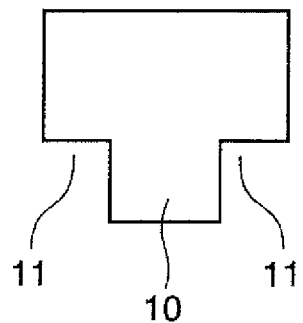
FIG. 11 shows patterns of protrusions and cutouts of the connecting terminal section of the biosensor.
Figures 2, 11:
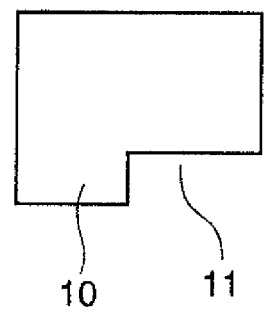
Figures 3, 11:
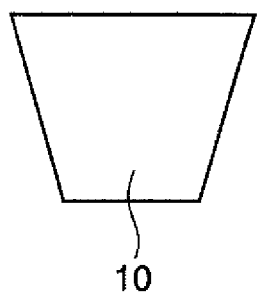
Figures 4, 11:
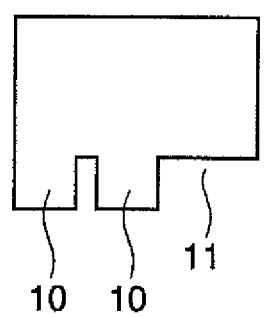

FIG. 11 shows examples of patterns of the protrusions and the cutouts. In FIG. 11, FIGS. 11-1 to 11-3 are examples having one protrusion, and FIG. 11-4 is an example having two protrusions.

In the biosensor container assembly of the claimed invention, a plurality of biosensors is contained in the container. Although the number of biosensors contained is not limited specifically, the number is typically 5 to 50. The biosensors are contained with their protrusions at the longitudinal end facing the bottom of the container. As such, while the contained biosensors basically overlap with each other and stand along the longitudinal direction, some may stand upright and some may incline to the left or right (see FIG. 5).

Figure 14:
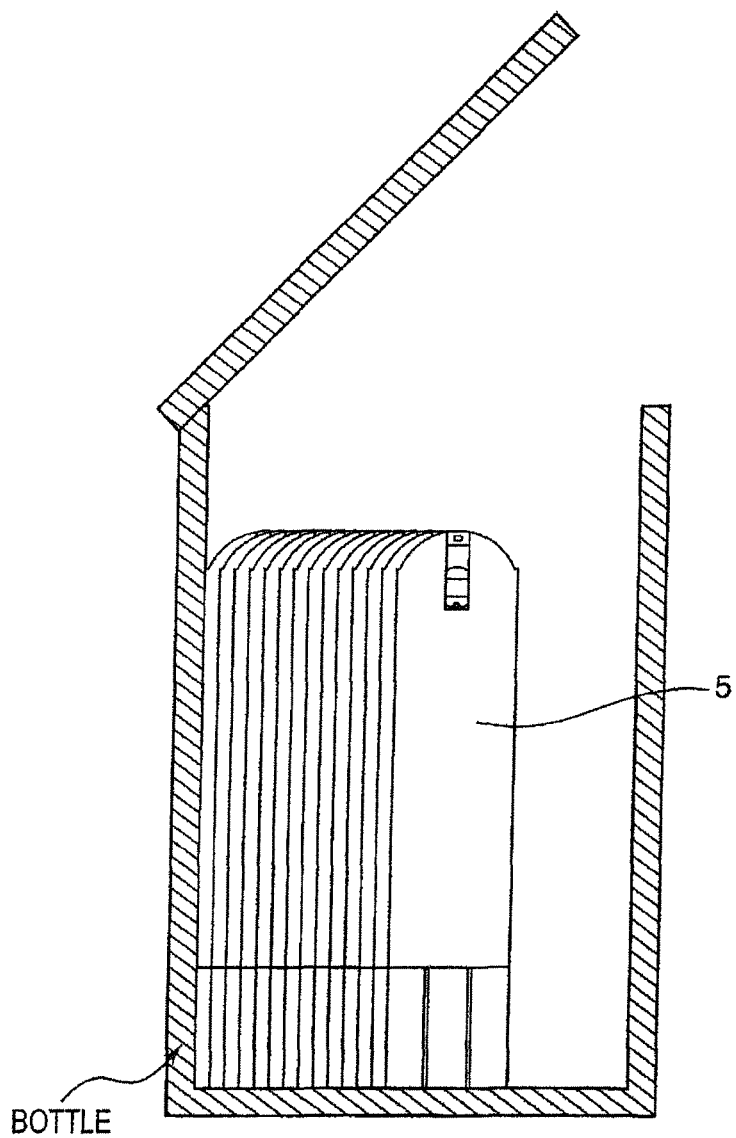
FIG. 14 is a sectional view showing a state where a plurality of conventional biosensors are contained in a container.
Figure 15:
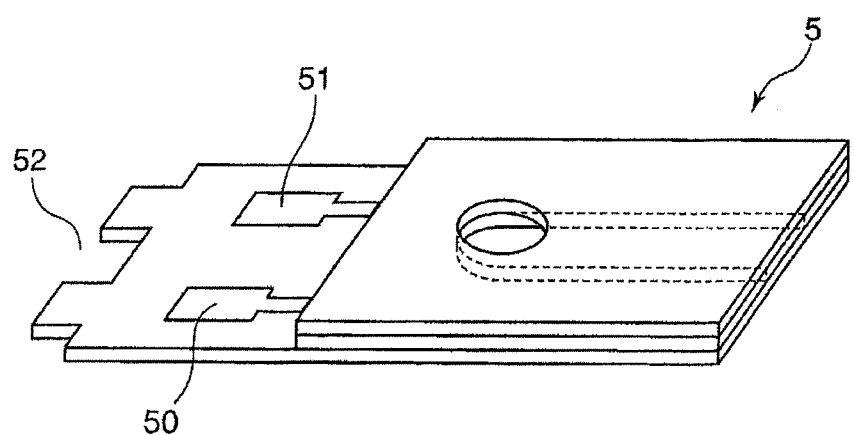
FIG. 15 is a front view of a second conventional biosensor.

Generally, a plurality of plate-shaped members, such as the biosensors, contained in the container tends to overlap completely with each other (see FIG. 14). It is often troublesome to pick up one biosensor among the completely overlapped plate-shaped biosensors from the container. On the other hand, while the biosensors contained in the biosensor container assembly of the claimed invention overlap with each other, they do not completely overlap and are oriented in random directions. Thus, a user can readily pick up one biosensor at a time.

Figure 6A:
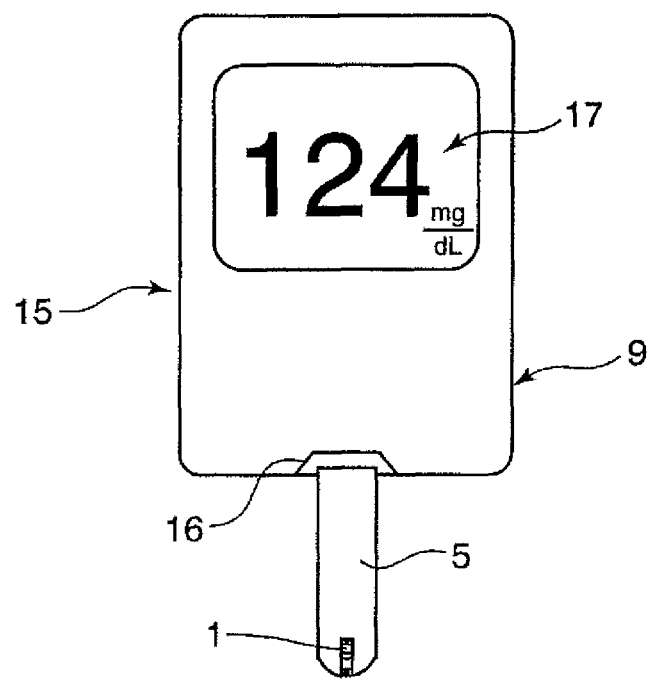

The biosensor of the claimed invention is mounted to the measuring apparatus to be used for measuring a specific component in the sample. Mounting to the measuring apparatus includes electrically connecting each terminal of the connecting terminal section of the biosensor to the measuring apparatus. FIG. 6A shows a state where the biosensor is mounted to the measuring apparatus.

As shown in FIG. 6A, the measuring apparatus has an insertion opening into which the biosensor is inserted, a measuring section that measures a specific component by means of the output from the measuring section of the biosensor, and a display section that displays the measured results.

As shown in FIG. 6A, the biosensor is inserted with the connecting terminal section facing the measuring apparatus, and the measuring section is preferably exposed from the measuring apparatus.

Figure 6B:
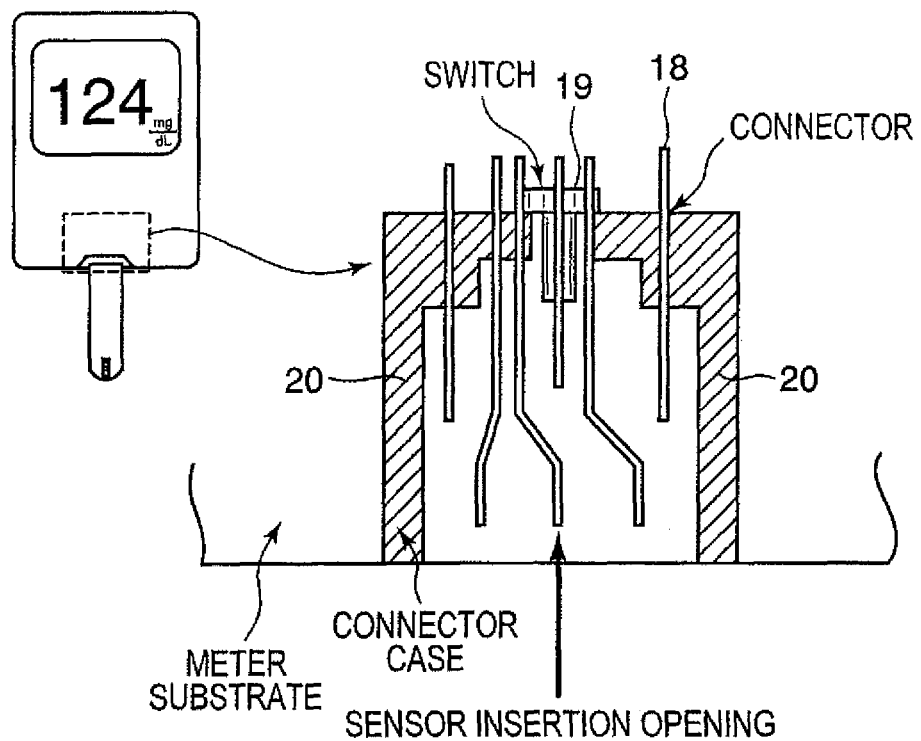
FIG. 6B shows a connector case provided inside the measuring apparatus.

FIG. 6B shows the inside of the apparatus around the insertion opening of measuring apparatus 9 having biosensor 5 inserted therein. As shown in FIG. 6B, measuring apparatus 9 has connector case 20 for receiving biosensor 5 inserted through the insertion opening. Within measuring apparatus 9, there are disposed connectors 18 for connection to the terminals of connecting terminal section 2 of biosensor 5 received in connector case 20 (FIG. 6B shows eight connectors 18). Moreover, switching section 19 is provided at the most inward part of connector case 20. When biosensor 5 is inserted into measuring apparatus 9 through the insertion opening, protrusion 10 can press switching section 19 to turn the switch on.

Figure 7:
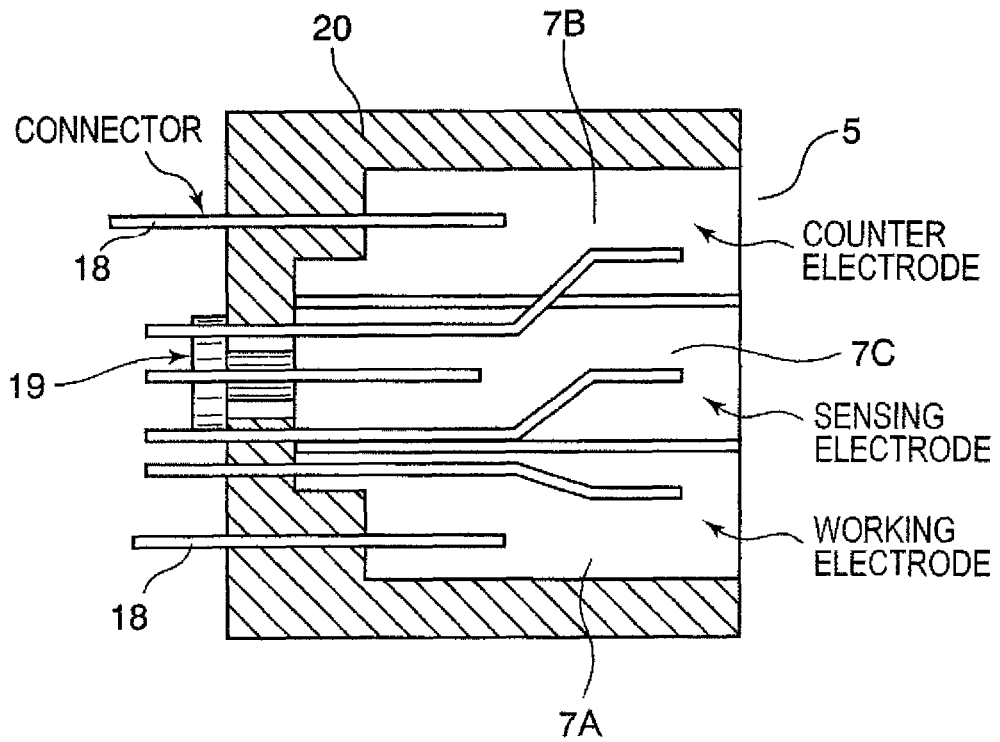
FIG. 7 is an enlarged sectional view showing a portion around a switching section of the measuring apparatus of FIGS. 6A and 6B.
Figure 8:
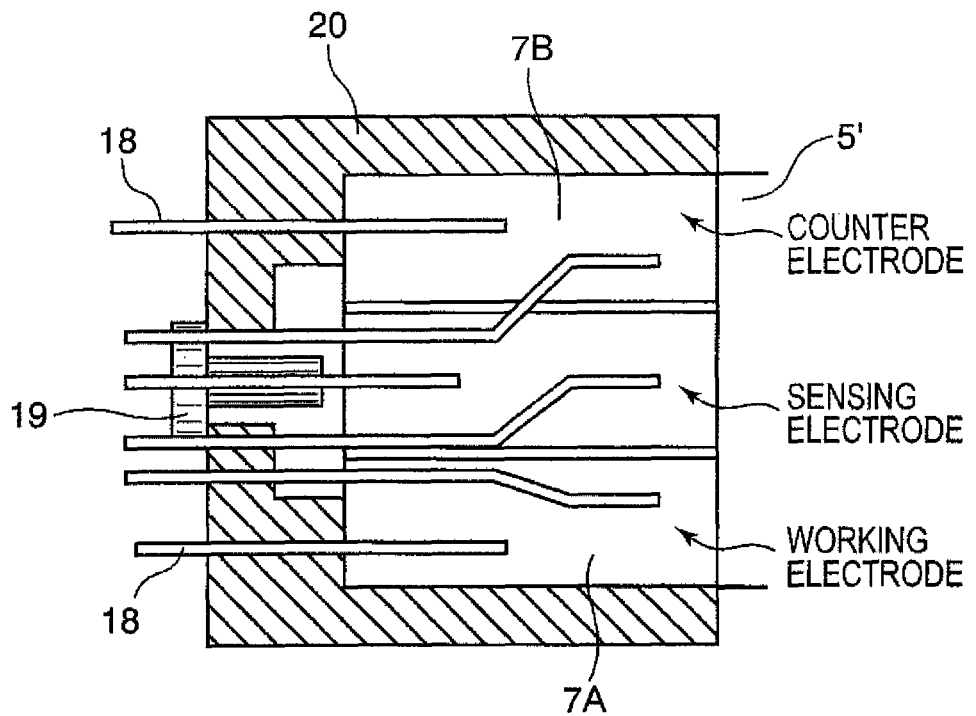
FIG. 8 is an enlarged sectional view showing a portion around the switching section of the measuring apparatus of FIGS. 6A and 6B.

FIG. 7 shows a state where the biosensor having the protrusion has pressed the switch placed inside the insertion section to turn the switch on. On the other hand, FIG. 8 shows a state where the biosensor having no protrusion has not pressed the switch placed inside the insertion section so that the switch remains off.

In this manner, the switch turns on or remains off depending on the presence/absence of the protrusion of the bio sensor inserted into the measuring apparatus, so that the type of inserted biosensor is identified based on the on/off of the switch. This prevents the false measured results from being displayed on the display section.

Hereinbelow, exemplary embodiments of the bio sensor container assembly and the measuring apparatus of the claimed invention will be described with reference to the accompanying drawings. As the biosensor, a blood glucose sensor for measuring blood sugar (glucose) level will be exemplified.

Embodiment 1

FIGS. 1A and 1B show blood glucose sensor 5. FIG. 1A is a front view of blood glucose sensor 5. Blood glucose sensor 5 has measuring section 1, connecting terminal section 2, and connecting section 3. Measuring section 1 is positioned at one end in the longitudinal direction of blood glucose sensor 5, while connecting terminal section 2 is positioned at the other end in the longitudinal direction of blood glucose sensor 5. FIG. 1B is an exploded perspective view of blood glucose sensor 5, Blood glucose sensor 5 is composed of cover 21, spacer 25, and base 30.

FIG. 2 shows an enlarged view of measuring section 1. Measuring section 1 has blood inlet 1A, blood guide path 1B, reagent layer 1C, and a pair of electrodes composed of a working electrode and a counter electrode (not shown). The working electrode and the counter electrode are an electrode pattern drawn on base 30.

FIG. 3 shows an enlarged view of connecting terminal section 2. Connecting terminal section 2 has connecting terminals 7A and 7B respectively connected to the pair of electrodes, and connecting terminal 7C connected to a sensing electrode. Connecting terminals 7A, 7B, and 7C are each connected with connectors 18 of the measuring apparatus (see FIG. 7).

Connecting section 3 is a member that electrically connects measuring section 1 with connecting terminal section 2. Specifically, connecting section 3 includes interconnects patterned on base 30.

Blood is introduced into guide path 1B through inlet 1A of measuring section 1 to dissolve reagent layer 1C. This provides a potential difference between the pair of electrodes (i.e., the working electrode and the counter electrode). By measuring the current flowing through the blood that has dissolved reagent layer 1C, the glucose concentration or the like in the blood is measured.

Blood glucose sensor 5 of the present embodiment can be characterized by the shape of its longitudinal end, i.e. the shape of connecting terminal section 2. As shown in FIG. 3, connecting terminal section 2 of blood glucose sensor 5 is provided with protrusion 10 and cutout 11. Protrusion 10 is disposed at a longitudinal end of connecting terminal section 2 of blood glucose sensor 5 at the center in the lateral direction thereof. In addition, protrusion 10 preferably protrudes along the direction to insert the biosensor into the measuring apparatus (see FIG. 6). Meanwhile, cutouts 11 are disposed on both sides of protrusion 10.

Blood glucose sensor 5 is contained in container 12 shown in FIG. 4 for storage. Container 12 includes close-ended tubular container body 13 and lid 14 that covers the opening of container body 13 in an openable/closable manner. Container body 13 is preferably tubular, but may be cylindrical, rectangular tubular or other shape.

Lid 14 is a member that air-tightly seals the opening of container body 13. Lid 14 may be integrated with container body 13 or formed as a separable member.

Figure 5:
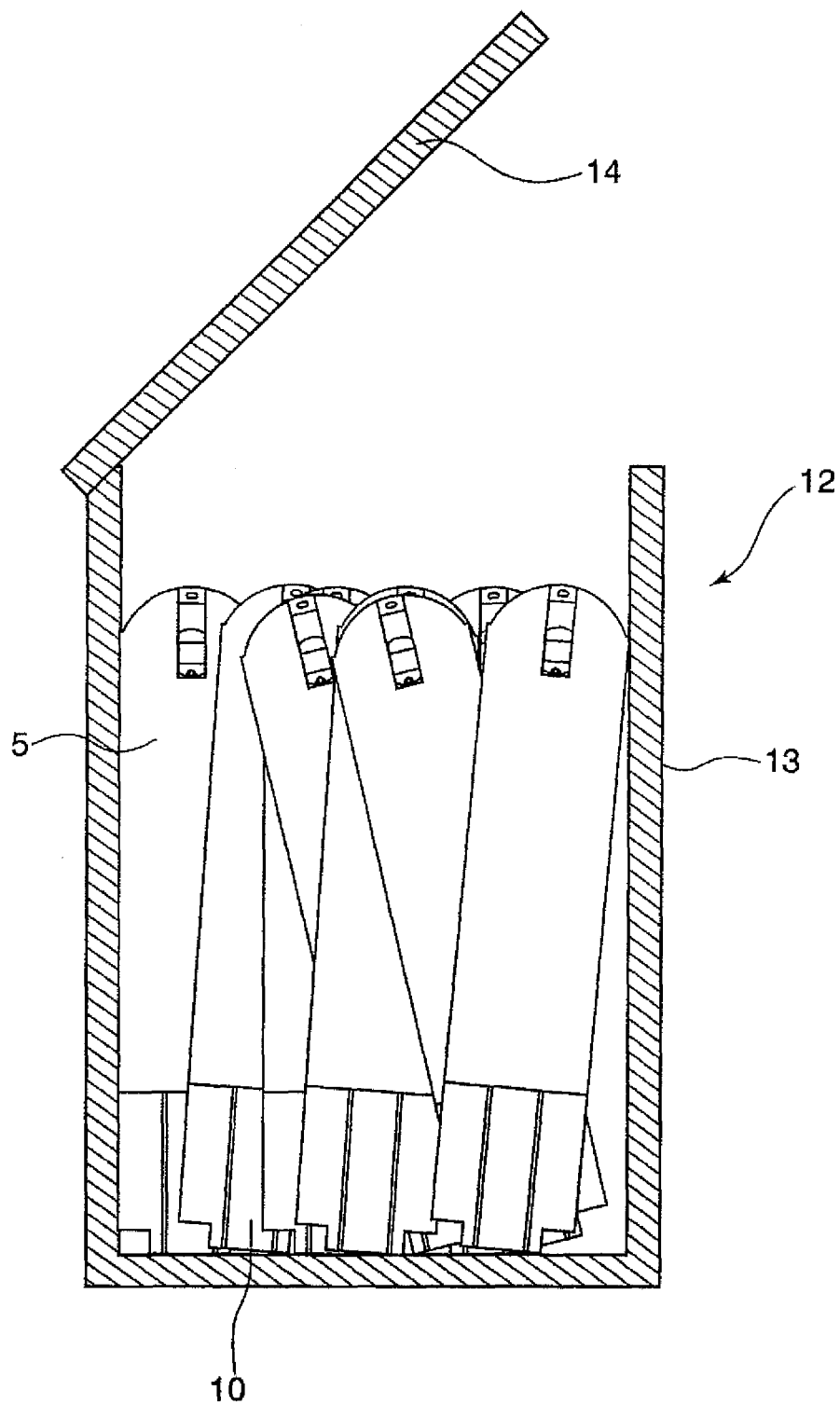
FIG. 5 is a sectional view showing a state where a plurality of blood glucose sensors of FIGS. 1A and 1B are contained in the container.

FIG. 5 shows a state where a plurality of blood glucose sensors 5 is contained in container 12. As shown in FIG. 5, blood glucose sensors 5 are contained in container 12, standing along the longitudinal direction. Blood glucose sensors 5 are also contained with their connecting terminal sections 2 having protrusion 10 facing the bottom of container 12. As such, a plurality of blood glucose sensors 5 is contained randomly in container 12 without completely overlapping with each other. The term "contained randomly" means a state where some of the blood glucose sensors 5 stand upright while some of them incline to the left or right.

Since the plurality of blood glucose sensors 5 is contained randomly, one of blood glucose sensors 5 can be picked up readily from container body 13. This improves the usability for the user.

As described above, in order for blood glucose sensors 5 to be placed randomly in container 12, the longitudinal end of blood glucose sensor 5 is preferably provided with protrusion(s) such as those shown in FIG. 11. For the pattern of FIG. 11-1, cutouts 11 are provided on both sides of protrusion 10, that helps the sensors to be contained randomly in the container, and the protrusions to be formed readily. For the pattern of FIG. 11-2, it helps the protrusions to be formed readily. The patterns of FIGS. 11-1 and 11-2 are simple in shape of the portions other than the protrusions. As such, laser patterning can be readily conducted on portions other than the protrusions. In addition, this helps the connectors to be disposed readily at the portion other than the protrusions as well. For the pattern of FIG. 11-3, the protrusion is less likely to be damaged due to the fracture, and it also helps to form the protrusions readily. This also helps to readily fabricate a connector case (described below) of a blood test apparatus contouring to the pattern of FIG. 11-3.

The pattern of FIG. 11-4 has two protrusions 10. When more than one protrusion is provided, all the protrusions are preferably disposed offset toward one side. In addition, by providing a plurality of protrusions, the more various types of blood sensor can be discriminated as described below.

One blood glucose sensor 5 picked up from container body 13 is inserted into measuring apparatus body 15 constituting measuring apparatus 9, as shown in FIG. 6A. FIGS. 6A and 6B show a state where blood glucose sensor 5 has been inserted into measuring apparatus body 15 through insertion opening 16 provided at the end of measuring apparatus body 15. Blood glucose sensor 5 is inserted into insertion opening 16 with connecting terminal section 2 facing insertion opening 16.

As shown in FIG. 6B, blood glucose sensor 5 inserted into measuring apparatus 9 is received in connector case 20 provided inside measuring apparatus body 15. Inside measuring apparatus 9, connectors 18 are disposed for connection to blood glucose sensor 5 received in connector case 20. In FIG. 6B six connectors 18 are shown, where connecting terminal 7A connected to the working electrode, connecting terminal 7B connected to the counter electrode, and connecting terminal 7C connected to the sensing electrode are each connected with two among the six connectors 18. By allowing each connecting terminal to be connectable with two among the connectors in this manner, each pattern of the conductive film (see FIG. 12) of connecting terminal section 2 can be discriminated via connectors 18. That is, the type of sensor can be discriminated.

Blood is introduced via inlet 1A into measuring section 1 of blood glucose sensor 5 inserted into measuring apparatus body 15 through insertion opening 16. As describe above, guide path 1B causes the capillary action, so that guide path 1B is filled with the blood by applying a droplet of blood on inlet 1A. As a result, reagent layer 1C dissolves in the blood.

Then, by applying a voltage between the pair of electrodes (the working electrode and the counter electrode), a current flows between the pair of electrodes corresponding to the blood glucose level. The working electrode and the counter electrode are respectively connected electrically to the terminals (7A, 7B) of the connecting terminal section via connecting section 3, so that the current is measured by the measuring section of measuring apparatus 9, thereby the blood glucose level is measured. Then, the measured blood glucose level is displayed on display section 17.

FIG. 7 shows connecting terminal section 2 of blood glucose sensor 5 inserted into measuring apparatus body 15 through insertion opening 16 and received in connector case 20. As shown in FIG. 7, six connectors 18 are disposed inside insertion opening 16 of measuring apparatus body 15. When blood glucose sensor 5 is inserted, connecting terminals 7A, 7B, and 7C of connecting terminal section 2 are each connected with two connectors 18.

Moreover, as shown in FIG. 7, the inward portion of connector case 20 is provided with switching section 19. Switching section 19 is pressed in and turned on by protrusion 10 provided on connecting terminal section 2 of blood glucose sensor 5 inserted into measuring apparatus body 15.

The type (such as product number) of blood glucose sensor 5 can be decided by the on/off state of switching section(s) 19. In this manner, protrusion 10 provided on connecting terminal section 2 can also function as the indication of the type of blood glucose sensor 5.

As shown in FIG. 8, switching section 19 is not pressed in by blood glucose sensor 5' without protrusion 10 inserted into measuring apparatus body 15 via insertion opening 16. Thus, switching section 19 remains off. In this manner, blood glucose sensor 5 with protrusion 10 and blood glucose sensor 5' without protrusion 10 are discriminated.

Discrimination of the Type of Sensor by Connector

As described above, the type of sensor can be discriminated by connector 18 of the blood test apparatus. As described above, the blood test apparatus is provided with six connectors 18. Thus, all the patterns of the conductive film of connecting terminal section 17, as shown in FIG. 12, can be discriminated via six connectors 18.

The specific method of discriminating the pattern of the conductive film of the connecting terminal section by means of connectors is described in Japanese Patent Application Laid-Open No. 2003-156469.

Figures 1, 12:
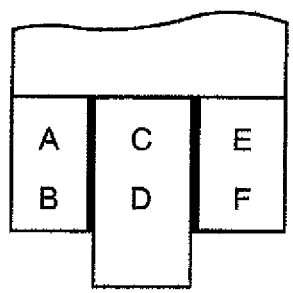
FIG. 12 shows patterning examples of a conductive film of the connecting terminal section of the biosensor.
Figures 2, 12:
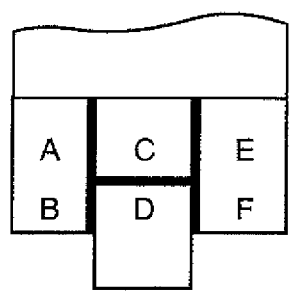
Figures 3, 12:
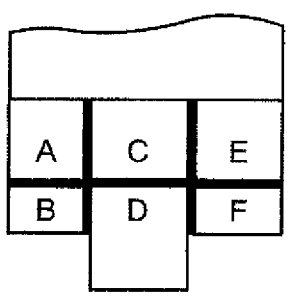
Figures 4, 12:
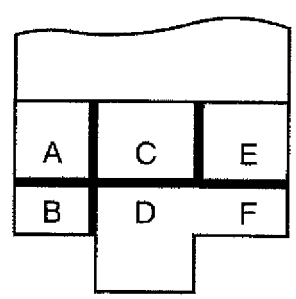
Figures 5, 12:
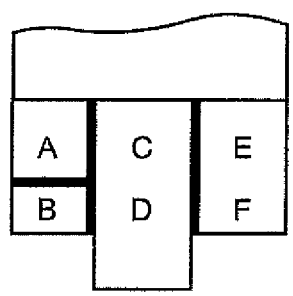
Figures 6, 12:
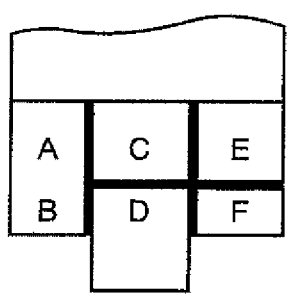
Figures 7, 12:
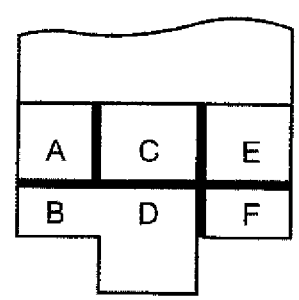
Figures 8, 12:
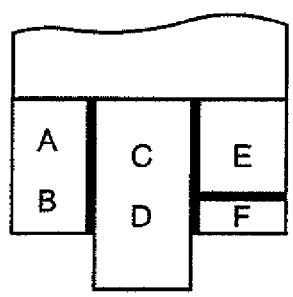
Figures 9, 12:
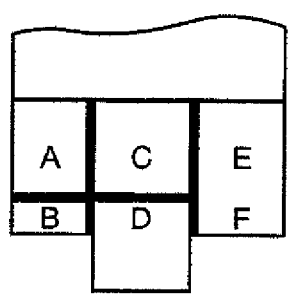
Figures 10, 12:
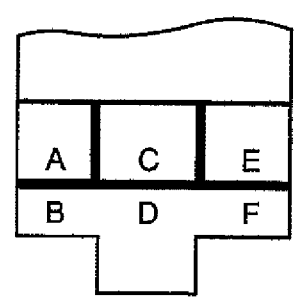
Figure 13:
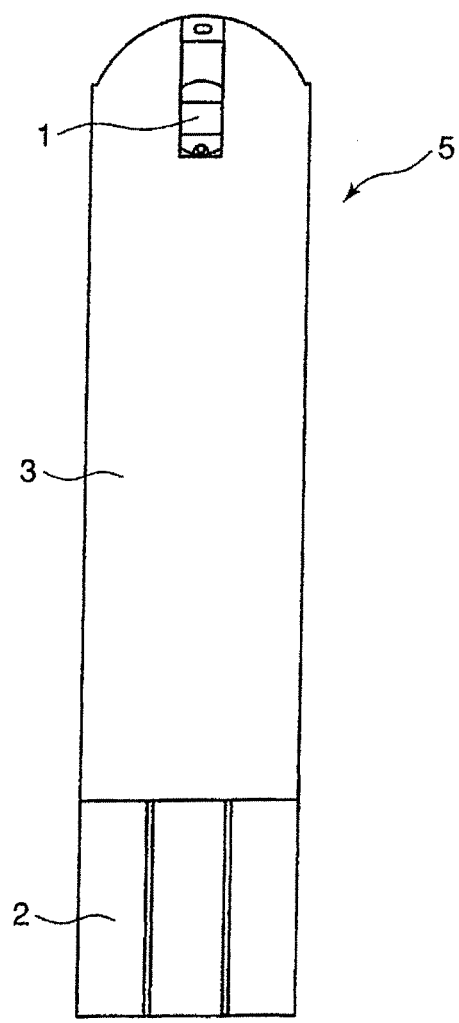
FIG. 13 is a front view of a first conventional biosensor.

Specifically, six connectors are respectively connected to positions A to F of connecting terminal section 2 as shown in FIG. 12. As a result, in FIG. 12-1, the connector connected to position A and the connector connected to position B, the connector connected to position C and the connector connected to position D, and the connector connected to position E and the connector connected to position F are conducted with each other. In contrast, in FIG. 12-2, the connector connected to position A and the connector connected to position B, and the connector connected to position E and the connector connected to position F are conducted with each other, while the connector connected to position C and the connector connected to position D are insulated from each other.

In this manner, all the sensors shown in FIG. 12 can be discriminated by six connectors 18.

Embodiment 2

Embodiment 1 described above illustrates an example where the measuring apparatus has one switching section 19. Embodiment 2 illustrates an example where the measuring apparatus has two switching sections 19.

Figure 9A:
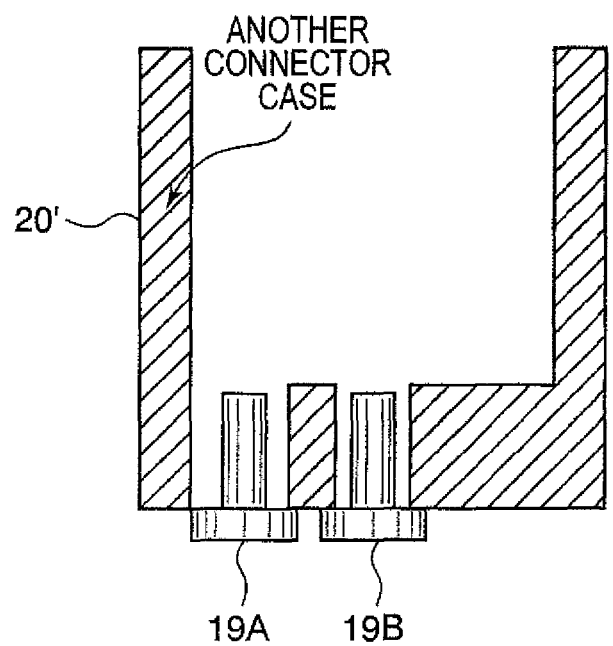
FIG. 9A shows a connector case having two switching sections.
Figure 9B:
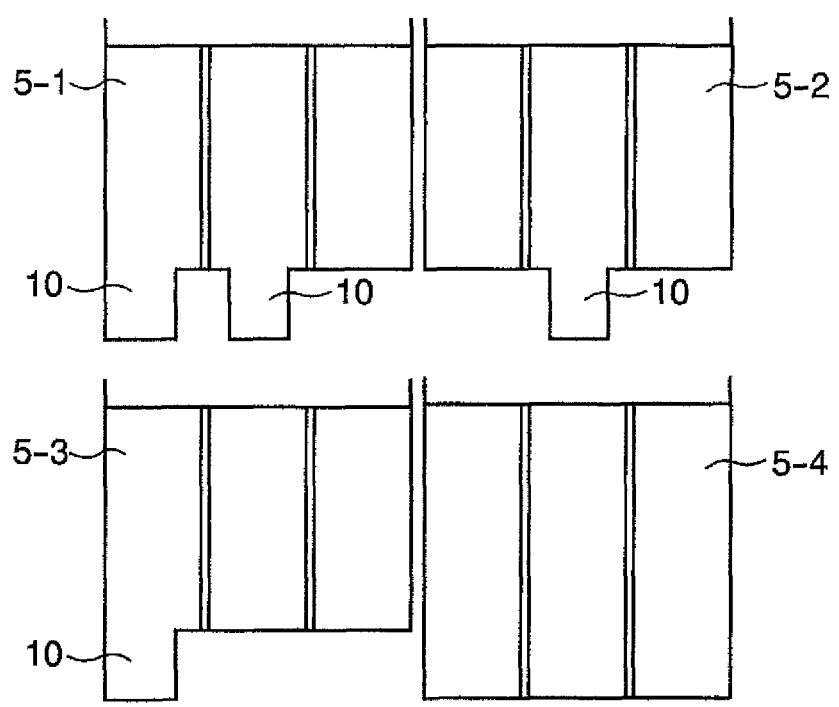
FIG. 9B shows four types of blood glucose sensors.

FIG. 9A shows connector case 20' of the measuring apparatus, connector case 20' being provided with two switching sections 19A and 19B. The following discusses a case where blood glucose sensors 5-1 to 5-4 having four different types of protrusion patterns as shown in FIG. 9B are inserted into connector case 20' of the measuring apparatus. Blood glucose sensor 5-1 has one protrusion 10 on the connecting terminal section, blood glucose sensors 5-2 and 5-3 have two protrusions 10 on connecting terminal section 2, and blood glucose sensor 5-4 has no protrusion 10 on connecting terminal section 2.

Figure 10A:
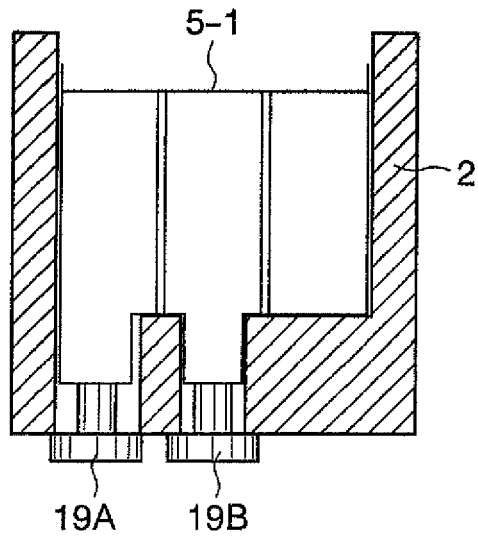
FIG. 10 shows states where the blood glucose sensors of FIG. 9B are inserted into the connector case of FIG. 9A.
Figure 10B:
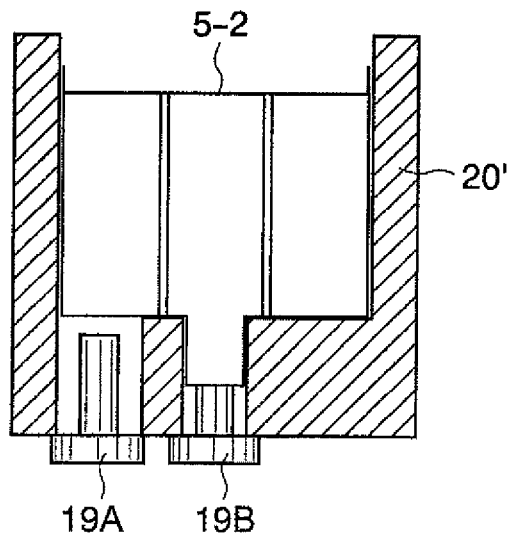
Figure 10C:
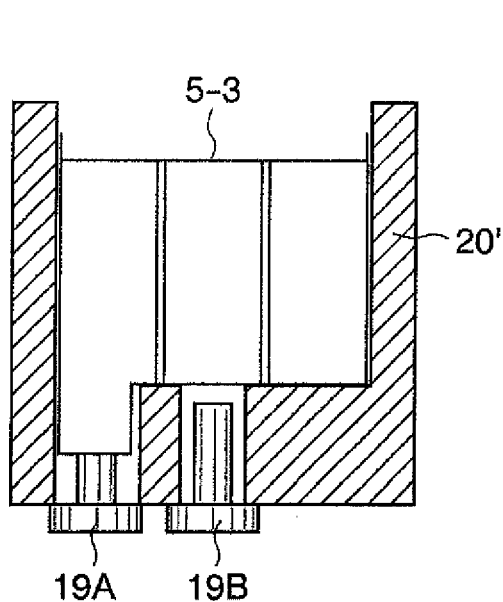
Figure 10D:
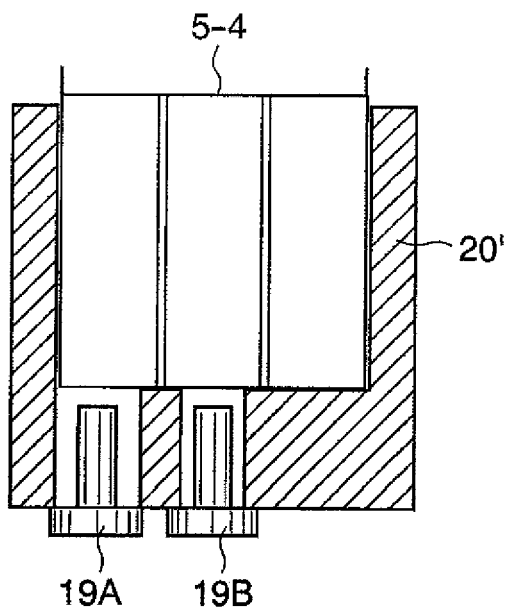

FIGS. 10A to 10D show a state where blood glucose sensors 5-1 to 5-4 are inserted into the measuring apparatus having connector case 20' as shown in FIG. 9A. FIG. 10A shows a case where blood glucose sensor 5-1 is inserted, and it can be found that two switching sections 19A and 19B are both pressed in by the protrusions so as to be turned on. FIG. 10B shows a case where blood glucose sensor 5-2 is inserted, and it can be found that one of two switching sections (19B) is pressed in by the protrusion so as to be turned on. FIG. 10C shows a case where blood glucose sensor 5-3 is inserted, and it can be found that the other of two switching sections (19A) is pressed in by the protrusion so as to be turned on. FIG. 10D shows a case where blood glucose sensor 5-4 is inserted, and it can be found that both of two switching sections 19A and 19B are not pressed in so as to remain off.

In the manner described above, it can be found that four blood glucose sensors 5-1 to 5-4 can be each discriminated by the two switches of the measuring apparatus.

As described above, the measuring apparatus with one switching section can discriminate twice as many types of sensors as compared to the measuring apparatus with no switching section, and further the measuring apparatus with two switching sections can discriminate four times as many types of sensors as compared to the measuring apparatus with no switching section.

INDUSTRIAL APPLICABILITY

The biosensor in the claimed invention has a protrusion at a longitudinal end. Thus, a plurality of biosensors is contained randomly in the biosensor container assembly of the claimed invention. Thus, the plurality of biosensors contained in the container can be readily picked up one at a time, improving the convenience for the user.

Moreover, the picked-up biosensor is used by being inserted into the measuring apparatus. At this time, the protrusion can turn on the switch of the measuring apparatus, so that the biosensor can be discriminated from one without protrusion. This also prevents the false measured results from being provided to the user.

REFERENCE SIGNS LIST 1 measuring section
1A inlet
1B guide path
1C reagent layer
2 connecting terminal section
3 connecting section
5, 5-1 to 5-4, 5' blood glucose sensor
7A, 7B, 7C connecting terminal
9 measuring apparatus
10 protrusion
11 cutout
12 container
13 container body
14 lid body
15 measuring apparatus body
16 insertion opening
17 display section
18, 18A, 18B connector
19, 19A, 19B switching section
20, 20' connector case
21 cover
25 spacer
30 base
50 working electrode
51 counter electrode
52 information carrier

The invention claimed is:

1. A measuring apparatus having an insertion opening configured to allow a biosensor to be inserted therein with connecting terminals of the biosensor facing the insertion opening, the biosensor comprising a pair of electrodes composed of a working electrode and a counter electrode disposed at one end, the connecting terminals disposed at the other end, a protrusion disposed at the other end, and patterns of conductive film on the protrusion and the connecting terminals, the measuring apparatus measuring a specific component based on an output from the pair of electrodes, the measuring apparatus comprising:

a connector connected to the connecting terminals when the biosensor is inserted;
   a display that displays a measured result obtained by the measuring apparatus; and
   a switch that is pressed by the protrusion to turn on,
   wherein the measuring apparatus is adapted to discriminate a type of the biosensor currently inserted into the measuring apparatus based on a combination of: an on/off state of the switch and connecting states of the connector resulting from an arrangement of the patterns of the conductive film.

2. The measuring apparatus according to claim 1 further comprising another switch that is pressed by the protrusion to turn on.

* * * * *